United States Patent
Dong et al.

(10) Patent No.: US 10,858,427 B2
(45) Date of Patent: Dec. 8, 2020

(54) MONOCLONAL ANTIBODY AGAINST BOTH IL-17A AND IL-17F AND USE OF THE SAME

(71) Applicant: Suzhou Kanova Biopharmaceutical Co., Ltd., Jiangsu (CN)

(72) Inventors: Chen Dong, Beijing (CN); Li Guo, Beijing (CN)

(73) Assignee: Suzhou Kanova Biopharmaceutical Co., Ltd., Jiangsu (CN)

( * ) Notice: Subject to any disclaimer, the term of this patent is extended or adjusted under 35 U.S.C. 154(b) by 0 days.

(21) Appl. No.: 16/491,297

(22) PCT Filed: Mar. 10, 2017

(86) PCT No.: PCT/CN2017/076278
§ 371 (c)(1),
(2) Date: Sep. 5, 2019

(87) PCT Pub. No.: WO2018/161340
PCT Pub. Date: Sep. 13, 2018

(65) Prior Publication Data
US 2020/0031919 A1    Jan. 30, 2020

(51) Int. Cl.
    *A61K 39/395*    (2006.01)
    *C07K 16/24*     (2006.01)
    *A61P 37/00*     (2006.01)
    *A61K 39/00*     (2006.01)

(52) U.S. Cl.
CPC ............ *C07K 16/244* (2013.01); *A61P 37/00* (2018.01); *A61K 2039/505* (2013.01); *C07K 2317/24* (2013.01); *C07K 2317/31* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| | | |
|---|---|---|
| CN | 101563098 A | 10/2009 |
| CN | 102083858 A | 6/2011 |
| CN | 102448493 A | 5/2012 |
| CN | 102458437 A | 5/2012 |
| CN | 104884473 A | 9/2015 |
| JP | 2009/519348 A | 5/2009 |
| JP | 2010/530357 A | 9/2010 |
| JP | 2011/519911 A | 7/2011 |
| WO | WO-2007/070750 A1 | 6/2007 |
| WO | WO-2007/106769 A2 | 9/2007 |
| WO | WO-2008/133684 A1 | 11/2008 |
| WO | WO-2009/130459 A2 | 10/2009 |
| WO | WO-2009/136286 A2 | 11/2009 |
| WO | WO-2014/161570 A1 | 10/2014 |
| WO | WO-2015/014979 A1 | 2/2015 |

OTHER PUBLICATIONS

Kuwabara et al. The Role of IL-17 and Related Cytokines in Inflammatory Autoimmune Diseases. Mediators Inflannnn. 2017; 2017: 3908061; Published online Feb. 20, 2017.*
Wang et al "Clinical Research of Anti-Interleukin-17 Antibody in the Treatment of Autoimmune Diseases" Chinese Journal of New Drugs vol. 25, pp. 2531-2536, 2016.
Extended Search Report issued in European Application No. 17 899 842.3 dated Aug. 6, 2020.
Search Report and Written Opinion issued in International Application No. PCT/CN2017/076278 dated Oct. 19, 2017.
Office Action issued in Japanese Application No. 2019-570,603 dated Sep. 1, 2020.

* cited by examiner

*Primary Examiner* — Dong Jiang
(74) *Attorney, Agent, or Firm* — Cesari and McKenna, LLP (57) ABSTRACT

Provided is an anti-IL 17 A/F antibody that binds to both IL-17A and IL-17F and inhibits the activities of both 1L-17A and IL-17F. The antibody comprises heavy chain CDRs 1-3 represented by SEQ ID NOs: 1-3 respectively and light chain CDRs 1-3 represented by SEQ ID NOs:4-6 respectively. The use of the antibody in the manufacture of a medicament for treating diseases associated with IL-17A and/or IL-17F in a subject, and the pharmaceutical composition comprising the antibody are also provided.

15 Claims, 5 Drawing Sheets

Specification includes a Sequence Listing.

MONOCLONAL ANTIBODY AGAINST BOTH IL-17A AND IL-17F AND USE OF THE SAME

CROSS-REFERENCE TO RELATED APPLICATIONS

This application is the National Stage of International Application No. PCT/CN2017/076278, filed Mar. 10, 2017, the content of which is being incorporated by reference in its entirety for all purposes.

FIELD OF INVENTION

The invention relates to antibodies against both IL-17A and IL-17F and use of the same. Specifically, the present invention provides an anti-IL17A/F antibody that binds to both IL-17A and IL-17F and inhibits the activities of both IL-17A and IL-17F, and the use of the antibodies.

BACKGROUND

There are six members in the interleukin 17 (IL-17) cytokine family, including IL-17A (commonly referred to as IL-17), IL-17B, IL-17C, IL-17D, IL-17E (also known as IL-25) and IL-17F. Among all the members, the biological function and regulation of IL-17A (CTLA-8, Swiss Prot Q16552) and IL-17F (Swiss-Prot #Q96PD4 SEQ ID #NP 443104) are best understood. These two cytokines share the strongest sequence homology (55% identity). The genes encoding IL-17A and IL-17F are close to each other on the same chromosome in both mouse and human, underscoring their shared patterns of expression (Wang X., et al., Immunity 2012; 36: 23-31.). Functionally, both IL-17A and IL-17F mediate pro-inflammatory responses, with certain differences depending on the type and site of inflammation (Ishigame H, et al., Immunity 2009; 30: 108-119; Yang X O, et al., J Exp Med 2008; 205: 1063-1075.). IL-25 has the least sequence similarity with IL-17A, only 16% compared with 50% in the case of IL-17F. Correspondingly, IL-25 plays distinct roles in immunity, mainly regulating the T helper (Th) 2 response against helminthic parasites and allergic inflammation (Fallon P G, et al., J Exp Med 2006; 203: 1105-1116.). IL-17B, IL-17C and IL-17D have been shown to induce the production of pro-inflammatory cytokines, but their biological function is largely unknown (Yamaguchi Y, et al., J Immunol 2007; 179:7128-7136; Wu Q, et al., Microbes Infect 2007; 9: 78-86; Li H, et al, Proc Natl Acad Sci USA 2000; 97: 773-778). Recent studies by three different groups highlighted the function of IL-17C in mucosal immunity and autoimmune responses (Ramirez-Carrozzi V, et al. Nat Immunol 2011; 12: 1159-1166; Song X, et al., Nat Immunol 2011; 12:1151-1158; Chang S H, et al., Immunity 2011; 35: 611-621.). IL-17 family cytokines mediate their biological functions via surface receptors on target cells. IL-17RA was the first identified IL-17 receptor, and four other IL-17R family members, IL-17RB, IL-17RC, IL-17RD and IL-17RE, were subsequently identified, mainly based on their sequence similarity with IL-17RA. Functional receptors for IL-17 family cytokines often exist in the form of heterodimers, with IL-17RA as a common subunit. For example, the receptor complex consisting of IL-17RA and IL-17RC recognizes IL-17A and IL-17F, whereas IL-17RA pairs with IL-17RB, followed by binding to IL-25 (Iwakura Y, et al., Immunity 2011; 34: 149-162; Chang S H, Dong C. Cell Signal 2011; 23: 1069-1075.).

Dysregulated IL-17A and IL-17F production can result in excessive pro-inflammatory cytokine expression and chronic inflammation, which lead to tissue damage and autoimmunity. IL-17 family cytokines have been linked to many autoimmune diseases, including multiple sclerosis (MS), rheumatoid arthritis (RA), inflammatory bowel disease and psoriasis. MS, for a long time, was considered as a Th1-dependent disease, until studies revealed the key role of Th17 cells and IL-17 family cytokines in the development of MS using EAE, a mouse model resembling human MS (Langrish C L, et al., J Exp Med 2005; 201: 233-240; Park H, et al., Nat Immunol 2005; 6: 1133-1141.). Th17 cells and associated cytokines are the major force that drives the related central nervous system inflammation and lesion formation (Langrish C L, et al., J Exp Med 2005; 201: 233-240; Park H, et al., Nat Immunol 2005; 6: 1133-1141). IL-17A is readily detected in the synovial fluids and synovium of RA patients (Chabaud M, et al., J Immunol 1998; 161: 409-414.). Several studies using mouse models of RA have demonstrated a key role for IL-17A in the progression of disease (Murphy C A, et al., J Exp Med 2003; 198: 1951-1957; Nakae S, et al., J Immunol 2003; 171: 6173-6177; Nakae S, et al. Proc Natl Acad Sci USA 2003; 100: 5986-5990; Lubberts E, et al., Arthritis Rheum 2004; 50: 650-659; Ruddy M J, et al., J Leukoc Biol 2004; 76: 135-144). A blockade of IL-17 after disease onset effectively prevents bone and cartilage erosion and reduces the severity of clinical symptoms (Lubberts E, et al., Arthritis Rheum 2004). The broad involvement of IL-17A in many autoimmune diseases makes this cytokine an ideal drug target. Indeed, humanized IL-17A antibodies have been developed for the treatment of RA, psoriasis and uveitis, with favorable outcomes (Genovesse M C, et al., Arthritis Rheum 2010; 62: 929-939; Hueber W, et al., Sci Transl Med 2010; 2: 52-72.).

Taken together, IL-17A and IL-17F have identical receptor and function redundantly in promoting inflammation. IL-17A and IL-17F can induce the production of multiple inflammatory cytokines, chemokines and adhesion molecules, and recruit neutrophils and macrophages to the inflammatory sites. Both IL-17A and IL-17F have been similarly implicated as contributing agents to progression and pathology of a variety of autoimmune disorders and inflammatory diseases in human and animal models of human diseases, including rheumatoid arthritis (RA), multiple sclerosis (MS), osteoarthritis and inflammatory bowel disorder (IBD). High level of IL-17A is detected in the synovial tissue of RA patients (Chabaud M et al., J Immunol 2003; 171: 6173-6177). IL-17A is over-expressed in the cerebrospinal fluid of MS patients (Hellings, P. W., et al., Am. J. Resp. Cell Mol Biol. 28 (2003)42-50).

SUMMARY OF INVENTION

The demonstrated immunological activities of both IL-17A and IL-17F illustrate the clinical or therapeutic potential of, and need for, IL-17A and IL17F antagonists. Specifically, antibodies that bind to both IL-17A and IL-17F and block the activities of both IL-17A and IL-17F would possess novel and/or improved therapeutic qualities. Thus, there is a need for an antagonist to both IL-17A and IL-17F. Blocking both IL-17A and IL-17F with a monoclonal antibody will have better clinical or therapeutic potential than IL-17A antagonist, which is used for the treatment of psoriasis, psoriatic arthritis and ankylosing spondylitis.

The present invention provides antibodies that are capable of specifically binding to both human IL-17A and IL-17F (herein referred to interchangeably as "cross-reactive antibodies", "IL-17A/F antibodies", etc.) and that are capable of modulating the activities of both IL-17A and IL-17F, and thus are useful in the treatment of various diseases and pathological conditions such as immune related and inflammatory diseases. The antibodies are characterized in comprising a CDR1H represented by SEQ ID NO: 1, CDR2H represented by SEQ ID NO: 2, CDR3H represented by SEQ ID NO: 3; and CDR1L represented by SEQ ID NO: 4, CDR2L represented by SEQ ID NO: 5 and CDR3L represented by SEQ ID NO: 6.

In one embodiment, such anti-IL17A/F antibody is a murine, chimeric or humanized variant. The anti-IL17A/F antibody is a monoclonal and bi-specific antibody.

In one embodiment, the antibody is characterized in comprising:
a variable heavy chain domain (VH1-1) represented by SEQ ID NO: 7, and a variable light chain domain (VL5) represented by SEQ ID NO: 8 or VL2-1 represented by SEQ ID NO: 9.

In one embodiment, the antibody is characterized in comprising:
a variable heavy chain domain (VH1-1) represented by SEQ ID NO: 7, and a variable light chain domain (VL5) represented by SEQ ID NO: 8.

In one embodiment, the antibody is characterized in being of human IgG class.

In one embodiment, the antibody is characterized in comprising:
a heavy chain represented by SEQ ID NO: 10, and
a light chain represented by SEQ ID NO: 11.

The IL-17A/F antibodies may find utility for, among other things, in vitro, in situ, or in vivo diagnosis or treatment of mammalian cells or pathological conditions associated with the presence of IL-17A and/or IL-17F. In one embodiment, the diseases associated with IL-17A and/or IL-17F are autoimmune disorders or inflammatory diseases, for example, including, but not limited to, psoriasis, psoriatic arthritis, ankylosing spondylitis, rheumatoid arthritis (RA), multiple sclerosis (MS), systemic lupus erythematosus, osteoarthritis or inflammatory bowel disorder (IBD).

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous without deviation from the scope of the present invention which is defined by the claims.

The practice of the present invention will employ, unless otherwise indicated, conventional techniques of molecular biology, chemistry, biochemistry and recombinant DNA technology, bioinformatics which are within the skill of the art. Such techniques are explained fully in the literature.

In the first aspect, the present invention provides an anti-IL17A/F antibody that binds to both IL-17A and IL-17F and inhibits the activities of IL-17A and IL-17F. The antibody comprises a CDR1H represented by SEQ ID NO: 1, CDR2H represented by SEQ ID NO: 2, CDR3H represented by SEQ ID NO: 3; and CDR1L represented by SEQ ID NO: 4, CDR2L represented by SEQ ID NO: 5 and CDR3L represented by SEQ ID NO: 6.

The anti-IL17A/F antibody of the present invention is a monoclonal antibody with bi-specific binding activity.

The anti-IL17A/F antibody can inhibit the binding of IL-17A and IL-17F to their receptors.

In one embodiment, such anti-IL17A/F antibody is a murine, chimeric or humanized variant. In one embodiment, the antibody comprises a variable heavy chain domain (VH1-1) represented by SEQ ID NO: 7, and a variable light chain domain (VL5) represented by SEQ ID NO: 8 or VL2-1 represented by SEQ ID NO: 9. In one embodiment, the antibody comprises a variable heavy chain domain (VH1-1) represented by SEQ ID NO: 7, and a variable light chain domain (VL5) represented by SEQ ID NO: 8.

In one embodiment, the antibody is characterized in being of human IgG class. In one embodiment, the humanized antibody comprises a heavy chain represented by SEQ ID NO: 10, and a light chain represented by SEQ ID NO: 11.

In the second aspect, the present invention provides a nucleotide sequence encoding the anti-IL17A/F antibody of the first aspect. As it is well known in the art, the nucleotide sequence may be codon-optimized, depending on the cell type to be used to express the anti-IL17A/F antibody.

The present application also provides a nucleotide sequence encoding a heavy chain variable domain and/or a light chain variable domain of the anti-IL17A/F antibody of the first aspect.

A recombinant expression vector comprising the nucleotide sequence encoding the anti-IL17A/F antibody of the first aspect is also within the scope of the present invention. The recombinant expression vector can express said nucleotide sequence in a prokaryotic or eukaryotic host cell.

As it is known in the art, a host cell comprising the expression vector or the nucleotide sequence encoding the anti-IL17A/F antibody of the first aspect is also within the scope of the present invention. The host cell can produce the anti-IL17A/F antibody of the present invention. The host cell can be obtained by transforming or transfecting the cell with the recombinant expression vector comprising the nucleotide sequence. The host cell may comprise the recombinant expression vector comprising the nucleotide sequence, or the nucleotide sequence may integrate into the genome of the host cell through homologous recombination. The host cell may be a prokaryotic or eukaryotic host cell, for example, a cell line derived from a mammal species, such as CHO cells, HEK293 cells, or myeloma cells and the like. The mammal species may be selected from, but not limited to, rat, mouse, monkey, or human. Preferably, the host cell is a human cell.

In this regard, the anti-IL17A/F antibody of the present invention can be expressed by the host cell comprising the expression vector or the nucleotide sequence encoding the anti-IL17A/F antibody of the first aspect. After expression, the anti-IL17A/F antibody can be recovered from said cell or the cell culture supernatant through conventional protein purification method. Recombinant production of antibodies is well-known is the art. In another aspect, the anti-IL17A/F antibody of the present invention can be synthetized or produced by immunizing animals with suitable antigens, and then recovering the anti-IL17A/F antibody from the ascites collected from the immunized animals.

In one embodiment, the present invention provides a method for producing the anti-IL17A/F antibody of the first aspect, wherein it comprises the following steps: expressing the anti-IL17A/F antibody by culturing the host cell comprising the expression vector or the nucleotide sequence encoding the anti-IL17A/F antibody of the first aspect, and recovering the anti-IL17A/F antibody from the host cell or the cell culture supernatant.

In the third aspect, the present invention relates to the use of the anti-IL17A/F antibody of the first aspect in the manufacture of a medicament for treating diseases associated with IL-17A and/or IL-17F in a subject. In one embodiment, the diseases associated with IL-17A and/or IL-17F are autoimmune disorders or inflammatory diseases, for example, including, but not limited to, psoriasis, psoriatic arthritis, ankylosing spondylitis, rheumatoid arthritis (RA), multiple sclerosis (MS), systemic lupus erythematosus, osteoarthritis and inflammatory bowel disorder (IBD). The subject may be a mammal, such as rat, mouse, monkey, or human. Preferably, the subject is human.

In the fourth aspect, the present invention provides a pharmaceutical composition for treating diseases associated with IL-17A and/or IL-17F in a subject, comprising a therapeutically effective amount of anti-IL17A/F antibody of the first aspect and pharmaceutically acceptable excipients. Those skilled in the art can select suitable excipients for the pharmaceutical composition. In one embodiment, the diseases associated with IL-17A and/or IL-17F are autoimmune disorders or inflammatory diseases, for example, including, but not limited to, psoriasis, psoriatic arthritis, ankylosing spondylitis, rheumatoid arthritis (RA), multiple sclerosis (MS), systemic lupus erythematosus, osteoarthritis and inflammatory bowel disorder (IBD). The subject may be a mammal, such as rat, mouse, monkey, or human. Preferably, the subject is human.

In the fifth aspect, the present invention provides a method for treating diseases associated with IL-17A and/or IL-17F in a subject, comprising the step of administrating a therapeutically effective amount of the pharmaceutical composition of the fourth aspect of the invention to the subject. In one embodiment, the diseases associated with IL-17A and/or IL-17F are autoimmune disorders or inflammatory diseases, for example, including, but not limited to, psoriasis, psoriatic arthritis, ankylosing spondylitis, rheumatoid arthritis (RA), multiple sclerosis (MS), systemic lupus erythematosus, osteoarthritis and inflammatory bowel disorder (IBD). The subject may be a mammal, such as rat, mouse, monkey, or human. Preferably, the subject is human.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"And/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The foregoing application, and all documents and sequence accession numbers cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

EXAMPLES

Example 1. Generation of Anti-IL17A/F Antibodies

BALB/c mice (16-18g, 6 weeks old, purchased from Beijing Vital River Laboratory Animal Technology Co., Ltd.) were immunized by subcutaneous injection with human IL-17A (Cell Signaling # 8928SF, www.cellsignal.com) and IL-17F (Cell Signaling # 8906LC, www.cellsignal.com) (each 10 μg) with complete Freund adjuvant (Sigma-Aldrich, Cat# F6881). Immunization was repeated 5 times at an interval of 3 days. 3 days after the final boost, the lymph nodes close to the injection site were carefully dissected out. The lymphocytes were fused with Ag8.653 myeloma cells (Sigma-Aldrich, Cat# 85011420) with PEG1500 (Polyethylene Glycol 1500, Roche T M. Cat#: 783641, 10×4ml in 75 mM Hepes, PEG 50% W/V) and cloned with HAT selection (Sigma cat#: H0262) and HFCS (Hybridoma Fusion and Cloning Supplement, 50×, Roche cat#: 11-363-735-001). The hybridoma supernatants were screened for the production of antibodies that can bind to both human IL-17A and IL-17F by ELISA and a cytokine release assay (see Example 5). The selected murine anti-IL17A/F clone (1-15-X) was humanized using CDR grafting and back mutation.

Antibody humanization by CDR grafting: A selection of acceptor frameworks was made. The variable domain sequences of parental antibody were searched in the database of human germline using NCBI Ig-Blast (http://www.ncbi.nlm.nih.gov/projects/igblast/). Five diverse human acceptors (i.e. human variable domains with high homology to the parental antibody) for each heavy chain and light chain were chosen. The CDRs of human acceptors were replaced with their mouse counterparts, resulting in the humanized variable domain sequences. The CDR sequences of heavy chain and light chain (SEQ ID NOs: 1-6) are shown below respectively. Five humanized heavy chains and five humanized light chains were designed, synthesized and inserted into an expression vector. The humanized antibodies were expressed, and then used for affinity ranking test. The antibodies with the strongest binding affinity (VH1-VL5 and VH1-VL2) were selected for back mutation. Among the variants, the VH1-1/VL5 and VH1-1/VL2-1 were selected for further characterization. VH1-1/VL5 showed the best binding affinity.

```
CDR1H amino acid sequence
                                    (SEQ ID NO: 1)
DYNLN CDR2H amino acid sequence
                                    (SEQ ID NO: 2)
VIHPDYGTTSYNQKFKD CDR3H amino acid sequence
                                    (SEQ ID NO: 3)
YDYGDAMDY CDR1L amino acid sequence
                                    (SEQ ID NO: 4)
RSSQSLVHSNGNTYLH CDR2L amino acid sequence
                                    (SEQ ID NO: 5)
KVSNRFS CDR3L amino acid sequence
                                    (SEQ ID NO: 6)
SQSTHVPLT Variable heavy chain domain (VH1-1) amino
acid sequence
                                    (SEQ ID NO: 7)
QFQLVQSGAEVKKPGASVKVSCKASGYTFTDYNLNWVRQAPGKG

LEWMGVIHPDYGTTSYNQKFKDRVTMTVDTSTSTVYMELSSLRS

EDTAVYYCVRYDYGDAMDYWGQGTLVTVSS

Variable light chain domain (VL5) amino
acid sequence
                                    (SEQ ID NO: 8)
DIVMTQSPLSLSVTPGQPASISCRSSQSLVHSNGNTYLHWYLQK

PGQPPQLLIYKVSNRFSGVPDRFSGSGSGTDFTLKISRVEAEDV

GVYYCSQSTHVPLTFGQGTKLEIK

Variable light chain domain (VL2-1) amino
acid sequence
                                    (SEQ ID NO: 9)
DIVMTQTPLSSSVTLGQPASISCRSSQSLVHSNGNTYLHWLQQR

PGQPPRLLIYKVSNRFSGVPDRFSGSGAGTDFTLKISRVEAEDV

GVYYCSQSTHVPLTFGQGTKLEIK
```

Example 2. Expression and Purification of Anti-IL17A/F Antibodies

Figure 1:
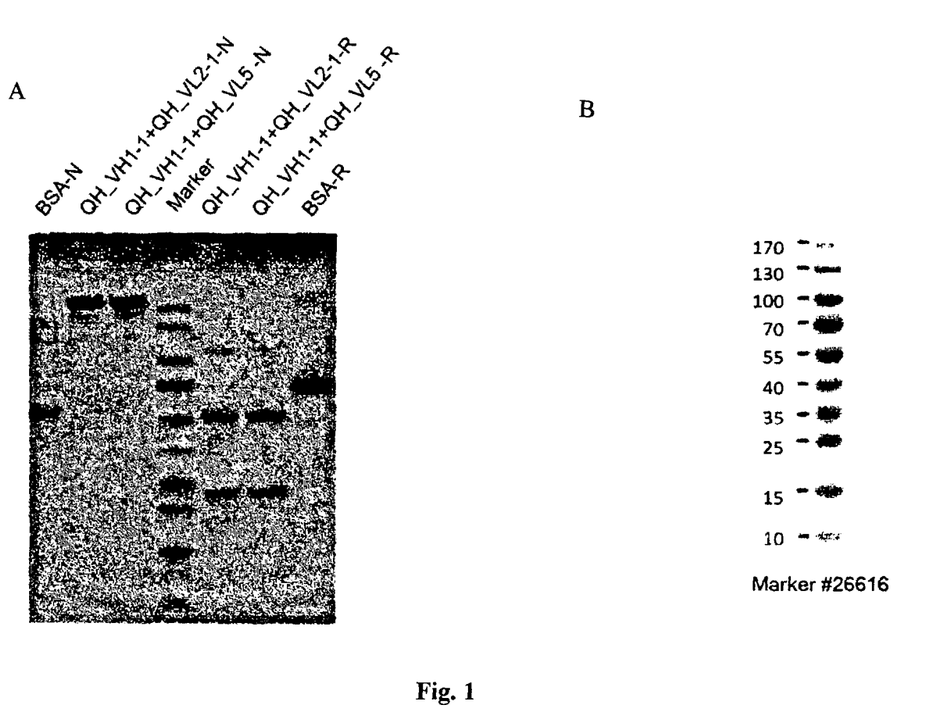
FIG. 1 shows SDS-PAGE result of parental antibody under non-reducing and reducing conditions. About 2 μg of protein was loaded in each lane. (A) Marker, page ruler pre-stained protein ladder (Thermo Scientific, Product No.: 26616); BSA-N, non-reduced; QH_VH1-1+QH_VL2-1-N, non-reduced; QH_VH1-1+QH_VL5-N, non-reduced; QH_VH1-1+QH_VL2-1-R, reduced; QH_VH1-1+QH_VL5-R, reduced; BSA-R, reduced; (B) The molecular weights shown in the Marker.

The DNA sequences encoding humanized IgG heavy chain (amino acid sequence of SEQ ID NO: 10) and light chain (amino acid sequence of SEQ ID NO: 11) were synthesized and inserted into pTGE5 vector (commercially available from Genescript) to construct expression plasmids of full-length IgGs. Expression of parental antibody was conducted in 100 ml HEK293 cell culture (HEK293 cell is commercially available from ThermoFisher Scientific) and the supernatants were purified with protein A affinity column. The purified antibody was buffer-exchanged into PBS using PD-10 desalting column (commercially available from Thermofisher Scientific). The concentration and purity of the purified protein were determined by OD280 and SDS-PAGE, respectively. The humanized antibodies were expressed in 30 ml HEK 293 cell culture. The cells were spun down. The supernatants were filtered and conducted with SDS-PAGE analysis (FIG. 1).

```
Heavy chain amino acid sequence comprising
VH1-1 (SEQ ID NO: 10, full length sequence)
QFQLVQSGAEVKKPGASVKVSCKASGYTFTDYNLNWVRQAPGKG

LEWMGVIHPDYGTTSYNQKFKDRVTMTVDTSTSTVYMELSSLRS

EDTAVYYCVRYDYGDAMDYWGQGTLVTVSSASTKGPSVFPLAPS

SKSTSGGTAALGCLVKDYFPEPVTVSWNSGALTSGVHTFPAVLQ

SSGLYSLSSVVTVPSSSLGTQTYICNVNHKPSNTKVDKKVEPKS

CDKTHTCPPCPAPELLGGPSVFLFPPKPKDTLMISRTPEVTCVV

VDVSHEDPEVKFNWYVDGVEVHNAKTKPREEQYNSTYRVVSVLT

VLHQDWLNGKEYKCKVSNKALPAPIEKTISKAKGQPREPQVYTL

PPSRDELTKNQVSLTCLVKGFYPSDIAVEWESNGQPENNYKTTP

PVLDSDGSFFLYSKLTVDKSRWQQGNVFSCSVMHEALHNHYTQK

SLSLSPGK
```

-continued

Light chain amino acid sequence comprising
VL5 (SEQ ID NO: 11, full length sequence)

DIVMTQSPLSLSVTPGQPASISCRSSQSLVHSNGNTYLHWYLQK

PGQPPQLLIYKVSNRFSGVPDRFSGSGSGTDFTLKISRVEAEDV

GVYYCSQSTHVPLTFGQGTKLEIKRTVAAPSVFIFPPSDEQLKS

GTASVVCLLNNFYPREAKVQWKVDNALQSGNSQESVTEQDSKDS

TYSLSSTLTLSKADYEKHKVYACEVTHQGLSSPVTKSFNRGEC

Example 3. SPR Analysis the Binding Affinity of Anti-IL17A/F Antibody to Human IL-17A and IL-17F Anti-human Fc gamma specific antibody (Jackson Immuno Research, Lot no. 124448, Code. 109-008-098) was immobilized onto the sensor chip using amine coupling method. Four antibodies secreted to the culture medium plus the parental antibody were injected and captured by anti-human Fc antibody via Fc (capture phase) individually. After equilibration, IL-17 was injected for 300 seconds (association phase) followed by the injection of running buffer for 1200s (dissociation phase). Responses of reference flow cell (flow cell 1) were subtracted from those of humanized antibodies flow cells during each cycle. The surface was regenerated before the injection of another humanized antibody. The process was repeated until all antibodies are analyzed. The off-rates of humanized antibodies were obtained from fitting the experimental data locally to 1:1 interaction model using the Biacore T200 evaluation software. The antibodies were ranked by their dissociation rate constants (off-rates, $K_d$). The binders that interact with IL-17 with similar affinity to parental antibody were selected.

TABLE 1

Affinity measurement data

| Ligand | Analyte | $k_a$ (1/Ms) | $k_d$ (1/s) | $K_D$ (M) | Rmax (RU) | Chi$^2$ (RU$^2$) | U-value |
|---|---|---|---|---|---|---|---|
| Chimeric IgG | IL-17 | 2.3E+06 | 4.2E−04 | 1.8E−10 | 66.35 | 0.779 | 1 |
| VH1-1 + VL2-1 | | 2.2E+06 | 1.8E−03 | 8.4E−10 | 52.3 | 1.65 | 4 |
| VH1-1 + VL5 | | 2.0E+06 | 5.9E−04 | 2.9E−10 | 60.19 | 0.741 | 1 |

Example 4. Binding to Human IL-17A and IL-17F Measured by ELISA

MaxiSorp 96-well plates (NUNC # 449824, www.thermofisher.com) were coated with 2 µg/ml human IL-17A (Cell Signaling # 8928SF, www.cellsignal.com) or human IL-17F (Cell Signaling # 8906LC, www.cellsignal.com) in 1× PBS (50 µl/well). Plates were incubated at 4° C. overnight. Coating solution was removed and plates were washed once with 200 µl/well PBST (1× PBS with 0.05% tween-20). Then 200 µl/well blocking buffer (1× PBS with 0.05% tween-20, 3% BSA) were added and incubated at room temperature for 1 hour. Blocking buffer was removed and plates were washed three times with 200 µl/well PBST (1× PBS with 0.05% tween-20). Anti-IL-17A/F antibody (produced in Example 2) was diluted to 10, 3.33, 1.11, 0.37, 0.123, 0.041, 0.0137, 0.0046, 0.0015, 0.00031, 0.000102, 0.000034 µg/ml by 1× PBS and added to plates (50 µl/well). Plates were incubated at room temperature for 2 hours. Antibodies in the wells were removed and plates were washed three times with 200 µl/well PBST (1× PBS with 0.05% tween-20). Goat anti-human IgG(H&L)—HRP secondary antibody (Jackson Immuno Research #109-035-088, www.jacksonimmuno.com) was diluted 1:5000 in 1× PBS and added to each well (50 µl/well). Plates were incubated at room temperature for 1 hour. Secondary antibody was removed and plates were washed seven times with 200 µl/well PBST (1× PBS with 0.05% tween-20). 50 µl/well TMB (eBioscience # 85-00-4201-56, www.ebioscience.com) was added and plates were incubated at room temperature for several minutes. Then 50 µl/well 2N $H_2SO_4$ was added to stop the reaction. Optical density was measured at 450 nm in relation to human IL-17A and IL-17F binding. The equilibrium constant, $EC_{50}$ (nM), was shown in Table 2. This result indicates that the anti-IL17A/F antibody can bind both human IL-17A and IL-17F with high affinity.

TABLE 2

| | Equilibrium constant, $EC_{50}$ (nM) | |
|---|---|---|
| | hIL-17A | hIL-17F |
| Anti-IL-17A/F antibody | 0.039 | 0.042 |

Example 5. Anti-IL17A/F Antibody Blocks Inflammatory Cytokine Production Stimulated by IL-17A, IL17F or IL17A/F Heterodimer The receptors for IL-17A and IL-17F are IL-17RA and IL-17RC respectively. These receptors are ubiquitously expressed on fibroblasts and epithelial cells. IL-17A and IL-17F can bind to the receptors on the cells and induce cells to produce and release multiple cytokines, such as IL-6, IL-8, and TNF-α. An IL-17A or IL-17F specific antibody can bind to the soluble IL-17A or IL-17F and block their binding to IL-17RA or IL-17RC respectively, thereby inhibiting the induction of cytokines, and further inhibiting the development of inflammation.

The assay is performed as detection of hIL-6 production of HFF-1 cells (human skin fibroblasts, Stem Cell Bank, Chinese Academy of Sciences, # SCSP-109) after hIL-17A, hIL-17F, or IL17-A/F heterodimer (R&D system Cat# 5837-IL) stimulation with pre-incubation of anti-IL-17A/F antibody (produced in Example 2). HFF-1 cells express IL-17 receptor on the cell surface. Soluble hIL-17A or hIL-17F binds to the receptor and induces HFF-1 cells to express and release hIL-6 cytokine. The anti-IL-17A/F antibody against hIL-17A and hIL-17F can block the binding of cytokines to IL-17 receptor and inhibit IL-17A/F-stimulated hIL-6 expression. hIL-6 released in the culture supernatant can be detected by ELISA. Measurement for hIL-6 can indicate the inhibition effect of the anti-IL-17A/F antibody.

Figure 2:
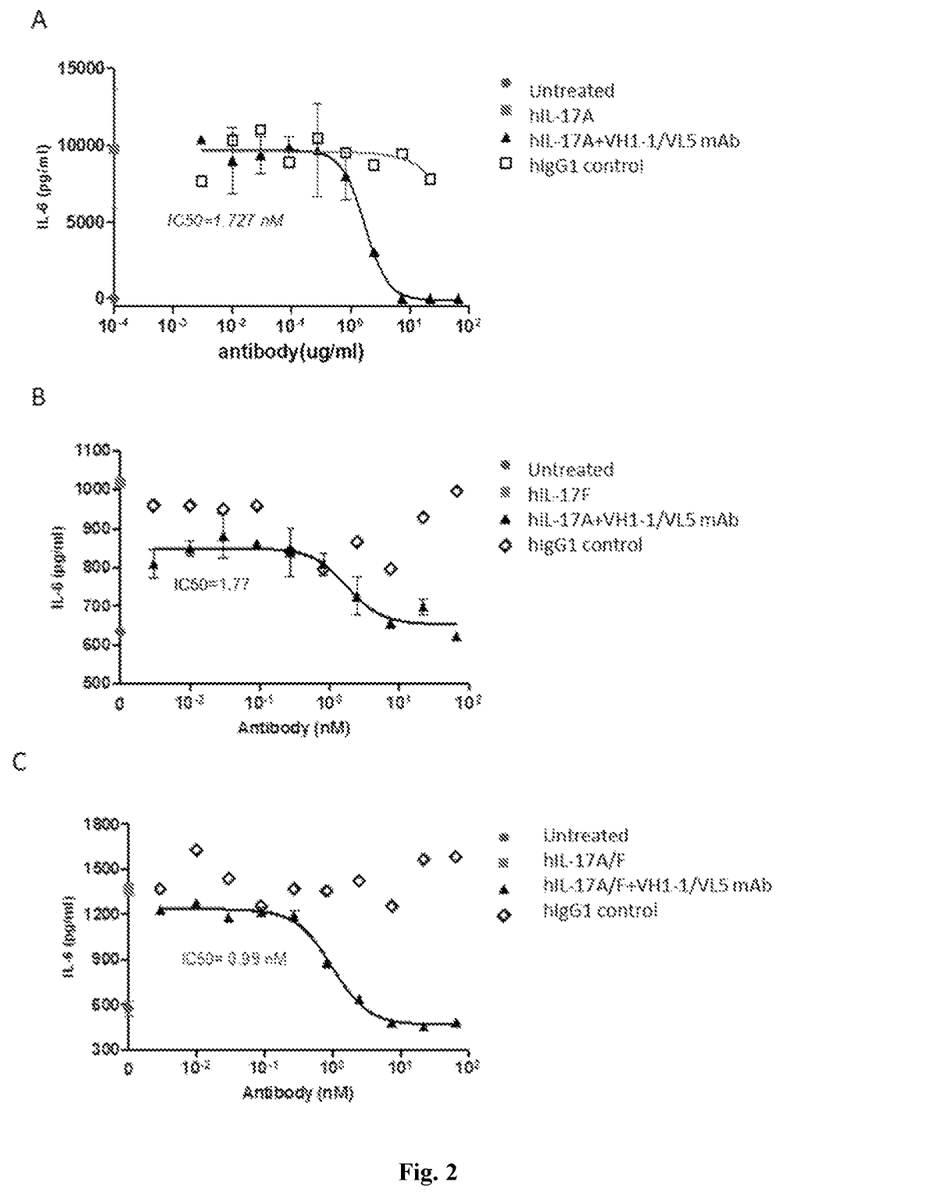
FIG. 2 shows the inhibitory effect (IC50 in nM) of anti-IL17A/F antibody on IL-6 induction by IL-17A, IL-17F and IL-17A/F in HFF-1 cells, i.e., the results of functional assay of the anti-IL17A/F antibodies of the present invention. (A) IL-17A-induced IL-6 production is inhibited by the anti-IL17A/F antibody, VH1-1/VL5 mAb, and IC50 is 1.727 nM; (B) IL-17F-induced IL-6 production is inhibited by the anti-IL17A/F antibody, VH1-1/VL5 mAb, and IC50 is 1.77 nM; (C) IL-17A/F heterodimer-induced IL-6 production is inhibited by the anti-IL-17A/F antibody, VH1-1/VL5 mAb, and IC50 is 0.99 nM. Human IgG1 (hIgG1) is used as a control antibody.

HFF-1 cells were seeded in 48-well plate with a cell density of $1.5 \times 10^5$ cells/well in 0.3 ml/well DMEM medium with 15% FBS (commercially available from ThermoFisher Scientific), 1% penicillin streptomycin (PS, commercially available from ThermoFisher Scientific) and incubated for 12 h at 37° C. and 5% $CO_2$. Then the medium in the wells was removed and the cells were washed once with PBS (300 µl/well). 300 µl/well serum-free DMEM medium was added to the cells and the cells were starved for 6 hours at 37° C. After 6 hours starvation, the serum-free DMEM medium in the wells was removed from cells. 150 µl/well DMEM medium with 30% FBS, 2% PS was added to the cells. Subsequently 150 µl/well mixture of anti-IL-17A/F antibody and hIL-17A, IL17F or IL-17A/F heterodimer was added to the corresponding wells. Plates were incubated for 24 hours at 37° C. Then the supernatants were harvested for hIL-6 ELISA. hIL-6 measurement was performed by using the kit of Human IL-6 ELISA Ready-SET-Go (eBioscience # 88-7066-88). Results was shown in FIG. 2, demonstrating that anti-IL17A/F antibody (VH1-1-VL5 mAb) blocks the stimulated IL-6 production induced by the cytokines, IL-17A, IL-17F and IL-IL17A/F heterodimer (FIG. 2, A, B and C).

Figure 3:
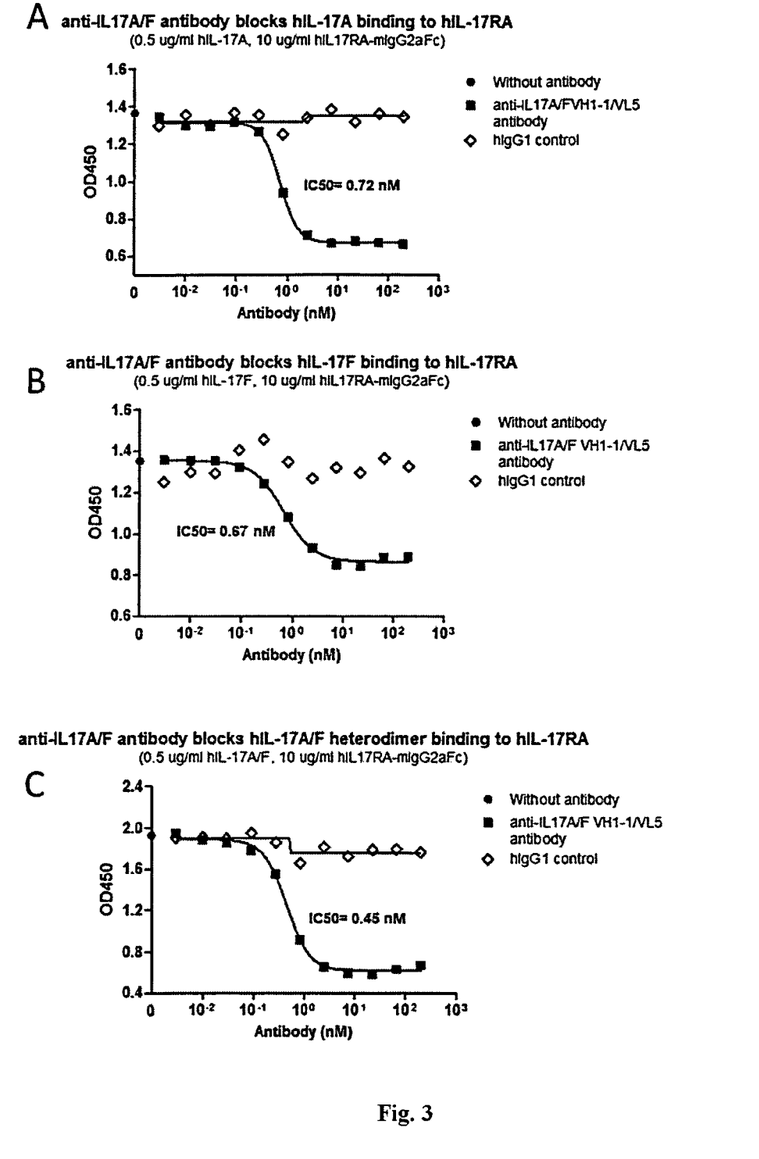
FIG. 3 shows the blocking effect of anti-IL17A/F antibody on the interaction between IL-17A, IL-17F or IL-A/F and IL-17 receptor. (A) The anti-IL17A/F antibody, anti-IL17A/F VH1-1/VL5 antibody, blocks the interaction between IL-17A and IL-17RA; (B) The anti-IL17A/F antibody, anti-IL17A/F VH1-1/VL5 antibody, blocks the interaction between IL-17F and IL-17RA; (C) The anti-IL17A/F antibody, anti-IL17A/F VH1-1/VL5 antibody, blocks the interaction between IL-17A/F and IL-17RA. Human IgG1 (hIgG1) is used as a control antibody.

Example 6. Anti-IL17A/F Antibody Blocks the Binding of IL-17A, IL-17F or IL17A/F to IL-17 Receptor The effect of the anti-IL17A/F antibody (produced in Example 2) on the binding of IL-17A, IL-17F or IL17A/F to the IL-17 receptor was tested by ELISA. IL-17A, IL-17F or IL-17A/F was coated in 96 well plate with 50 µl/well protein solution (protein concentration was 0.5 pg/ml) at 4° C. overnight. The wells were blocked with 1% BSA in PBST (tween 0.05%) by 200 µl/well at room temperature for 1 hour. The wells were washed 3 times with PBST. The anti-IL17A/F antibody and isotype control antibody human IgG1 (Biolegend cat# 403102) were diluted by PBS from 30 µg/ml down to 0.0005 µg/ml (30, 10, 3.33, 1.11, 0.37, 0.123, 0.041, 0.0137, 0.0046, 0.0015, 0.0005 pg/ml). The antibodies were added into the corresponding wells (50 µl/well) and incubated at room temperature for 4 hours. The wells were washed 3 times with PBST. hIL17RA-mIgG2aFc (10 µg/ml, in-house production according to standard molecular biology technology, Carson S, Molecular Biology Techniques, 2012) were added into each well (50 µl/well) and incubated at room temperature for 1 hour. The wells were washed 3 times with PBST. Goat anti-human IgG-HRP (1:5000 in PBS, EASYBIO Cat# BE0102) were added into each well (50 µl/well) and incubated at room temperature for 30 min. The wells were washed 6 times with PBST. TMB substrate was added into each well (50 µl per well) and the reaction was stopped by adding 50 µl of 2N $H_2SO_4$ to each well. The plate was read at 450 nm and 570 nm. As shown in FIG. 3, the anti-IL17A/F antibody blocks the binding of IL17A, IL17F and even IL-17A/F to IL-17 receptor. The data further demonstrate the anti-IL17A/F antibody inhibits the activity of IL-17A, IL-17F and IL17A/F by blocking the interaction between the cytokines and their receptor.

Figure 4:
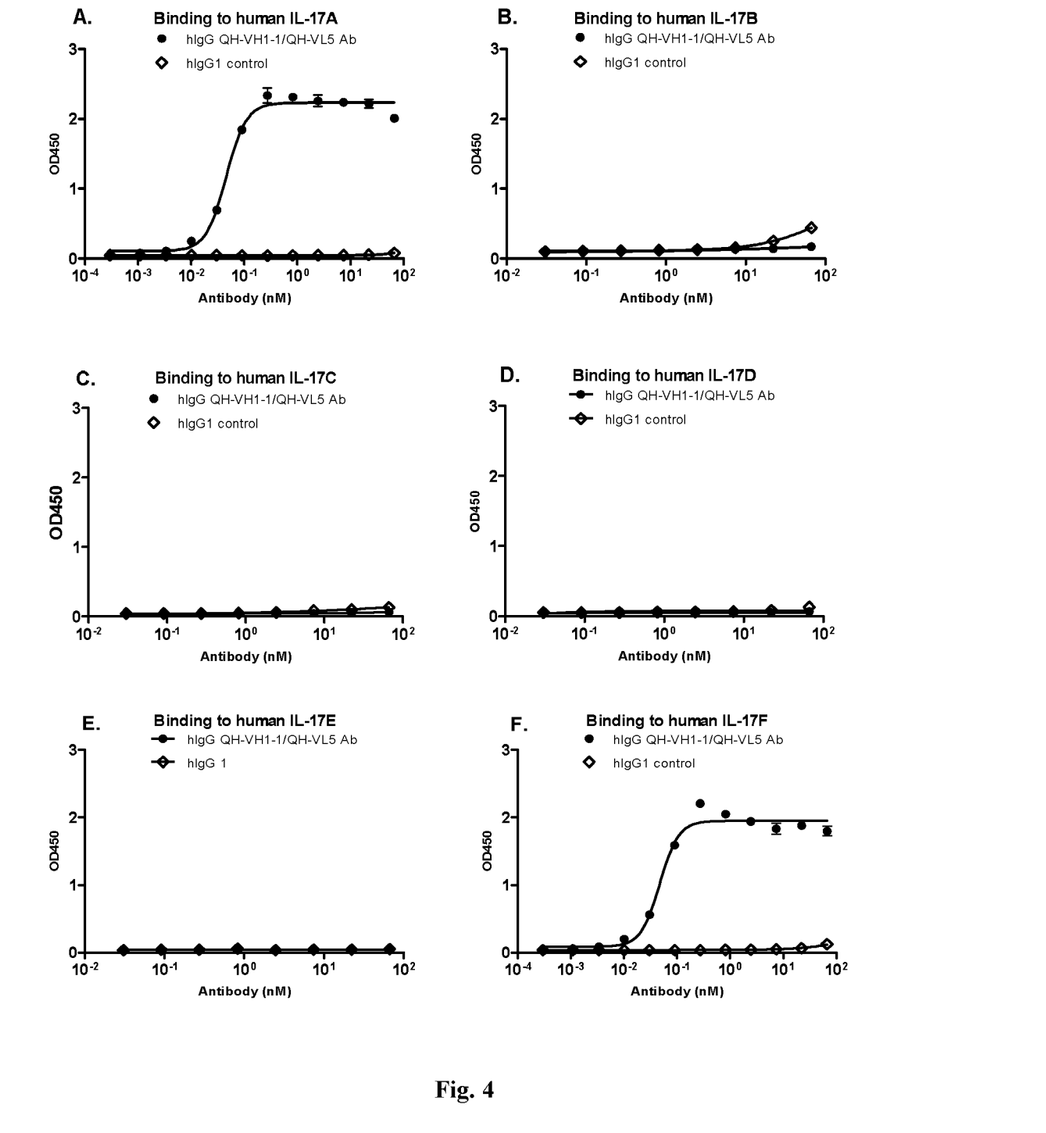
FIG. 4 shows the binding properties of hIgG VH1-1/VL5 to human IL-17 family members. 2 μg/ml of human IL-17A, B, C, D, E and F were coated to the ELISA plates respectively and incubated with serial concentrations of hIgG VH1-1/VL5 antibody (AF). Human IgG1 (hIgG1) was used as a control antibody. The binding properties were indicated by OD450 nm. EC50 values were calculated by GraphPad Prism.

Example 7. Binding to Human IL-17A, IL-17F and Cross-Reactivity with Other IL-17 Family Members Measured by ELISA MaxiSorp 96-well plates (NUNC # 449824, www.thermofisher.com) were coated with 2 µg/ml human IL-17A (Cell Signaling #89285F, www.cellsignal.com), human IL-17F (Cell Signaling #8906LC, www.cellsignal.com), human IL-17B (Peprotech #200-28, www.peprotech.com), human IL-17C (R&D systems #1234-IL-025/CF, www.rndsystems.com), human IL-17D ((Peprotech #200-27, www.peprotech.com), human IL-17E (R&D systems #1258-IL-025/CF, www.rndsystems.com) in 1× PBS (50 µl/well) respectively. Plates were incubated at 4° C. overnight. Coating solution was removed and plates were washed once with 200 µl/well PBST (1× PBS with 0.05% tween-20). Then 200 µl/well blocking buffer (1× PBS with 0.05% tween-20, 3% BSA) was added and incubated at room temperature for 1 hour. Blocking buffer was removed and plates were washed three times with 200 µl/well PBST (1× PBS with 0.05% tween-20). The anti-IL17A/F antibody, hIgG VH1-1/VL5, was diluted to 10, 3.33, 1.11, 0.37, 0.123, 0.041, 0.0137, 0.0046, 0.0015, 0.00031, 0.000102, 0.000034 µg/ml by 1× PBS and added to the plates (50 µl/well). Plates were incubated at room temperature for 2 hours. Antibodies in the wells were removed and plates were washed three times with 200 µl/well PBST (1× PBS with 0.05% tween-20). Goat anti-human IgG(H&L)—HRP secondary antibody (Jackson Immuno Research #109-035-088, www.jackson-immuno.com) was diluted 1:5000 in 1× PBS and added to each well (50 µl/well). Plates were incubated at room temperature for 1 hour. Secondary antibody was removed and plates were washed seven times with 200 µl/well PBST (1× PBS with 0.05% tween-20). 50 µl/well TMB (eBioscience # 85-00-4201-56, www.ebioscience.com) was added and plates were incubated at room temperature for several minutes. Then 50 µl/well 2N $H_2SO_4$ was added to stop the reaction. Plates were read at 450 nm. Results are showed in Table 3. The anti-IL17A/F antibody, hIgG VH1-1/VL5, has binding ability to both human IL-17A and 17F (FIG. 4, A and F) with EC50 of 0.046 and 0.047 nM respectively. Otherwise, hIgG VH1-1/VL5 do not bind to human IL-17B, 17C, 17D and 17E (FIG. 4, B, C, D and E). So, the hIgG VH1-1/VL5 antibody has binding specificity to human IL-17A and 17F and has no cross-reactivity to other IL-17 family members.

TABLE 3

Binding ability to IL-17 family members (EC50)

| Anti-IL-17A/F antibody | Binding $EC_{50}$ (nM) | | | | | |
| --- | --- | --- | --- | --- | --- | --- |
| | IL-17A | IL-17B | IL-17C | IL-17D | IL-17E | IL-17F |
| hIgGc VH1-1/VL5 | 0.046 | −0 | −0 | −0 | −0 | 0.047 |

Example 8. Cross-Reactivity with Cynomolgus IL-17A and IL-17F (Binding Assay)

The binding of anti-IL-17A/F antibody to cynomolgus IL-17A and IL-17F was determined by ELISA. Assay was performed in the same method of Example 7, except that cynomolgus IL-17A (Gene ID: XM_005552759.2, in-house production according to standard molecular biology method, Carson S, Molecular Biology Techniques, 2012) and IL-17F (Gene ID: XM_005552757.2, in-house production according to standard molecular biology method, Carson S, Molecular Biology Techniques, 2012) were used to replace human IL-17A and F, respectively.

Figure 5:
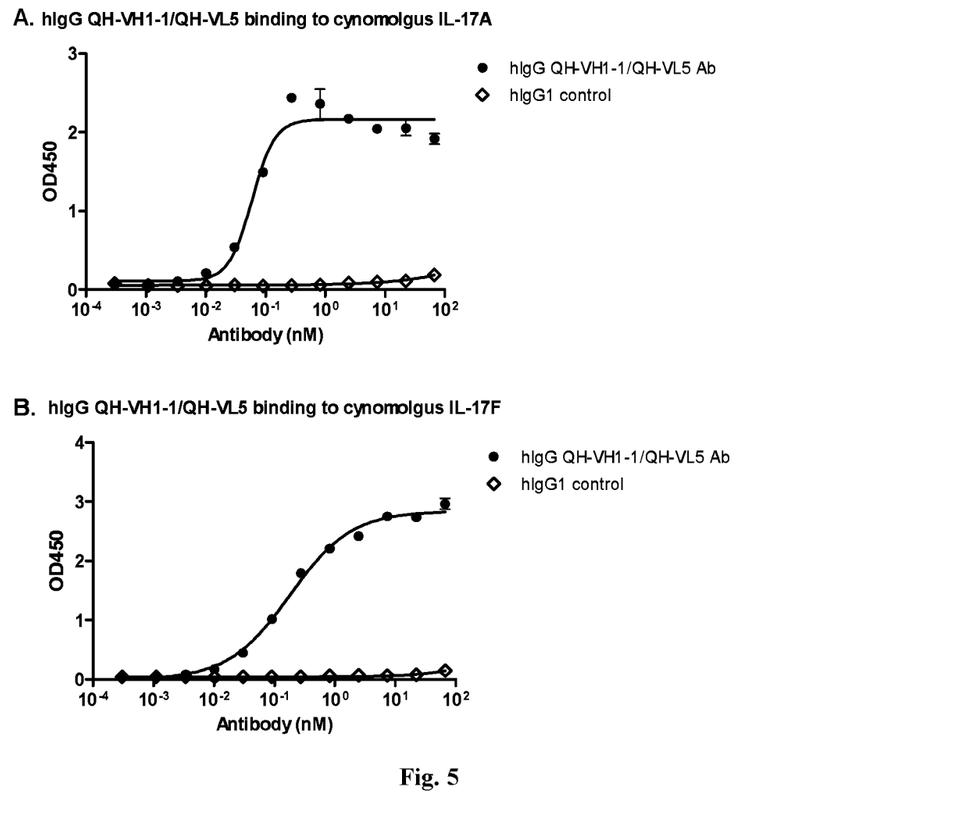
FIG. 5 shows the binding properties of hIgG VH1-1/VL5 to cynomolgus IL-17A and F. 2 μg/ml of Cynomolgus IL-17A (A) and 17F (B) were coated to ELISA plates respectively and incubated with hIgG VH1-1/VL5 antibody (with antibody concentration from 0.3 nM to 66.67 nM). Human IgG1 (hIgG1) was used as a control antibody. EC50 values were calculated by GraphPad Prism.

The hIgG VH1-1-VL5 antibody has binding ability to cynomolgus Il-17A and 17F with EC50 of 0.06 and 0.18 nM respectively (Table 4 and FIG. 5 A and B).

TABLE 4

| Anti-IL17A/F antibody | Binding ability to cynomolgus Il-17A and F (EC50) | |
|---|---|---|
| | Binding EC$_{50}$ (nM) | |
| | Cynomolgus IL-17A | Cynomolgus IL-17F |
| VH1-1-VL5 | 0.06 | 0.18 |

The cross-reactivity to cynomolgus IL-17A and IL-17F indicates that the cynomolgus monkey is qualified for pharmacokinetics, pharmacodynamics and toxicology studies of the anti-IL17A/F antibodies. It is advantageous to develop the anti-IL17A/F antibodies as a pharmaceutical composition.

Example 9. In Vivo animal Studies of the Effect of anti-IL17A/F Antibody

Figure 6:
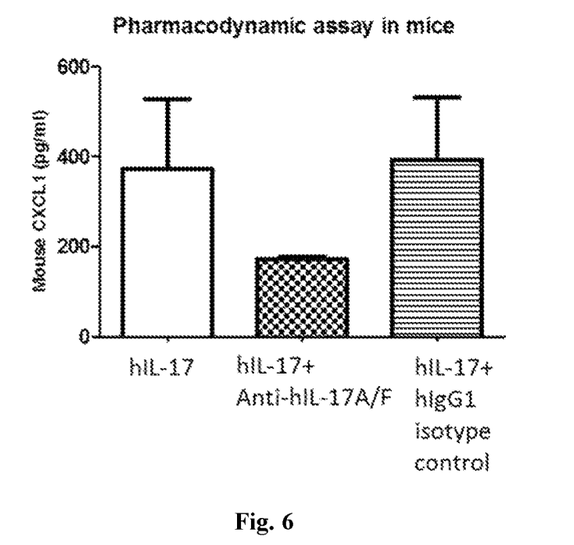
FIG. 6 The anti-IL17A/F antibody inhibits human IL-17-induced CXCL1 secretion in a mouse pharmacodynamics model. Human IL-17A (3 μg) was administered to mice subcutaneously (s.c.) 1 hour after intravenous (i.v.) injection of 20 μg anti-IL17A/F antibody per mouse. KC levels were determined by ELISA 2 hours after human IL-17A injection. n=5 mice per group.

The anti-IL-17A/F antibody (VH1-1/VL5 produced in Example 2, 20 μg/mouse) was administered intravenously to C57BL/6N mice (n=5 per group, 8 weeks old, body weight: 18-20g, commercially available from Beijing Vital River Laboratory Animal Technology Co., Ltd.) 1 hour prior to a subcutaneous injection of human IL-17 (Cell Signaling Cat# 8928SF, 3 pg per mouse). At 2 hours post-IL-17 administration, blood samples were collected, and CXCL1 chemokine level in the plasma was determined by ELISA (Mouse CXCL1/GRO alpha DuoSet ELISA kit, R&D system, DY345). Human IgG1 (BioLegend Cat# 40312) was used as an isotype control antibody. As shown in FIG. 6, the anti-IL17A/F antibody (produced in Example 2) was able to decrease human IL-17A-induced chemokines secretion in the plasma of the C57BL/6 mice as compared to the isotype control antibody. This result suggests that the anti-IL17A/F antibody could be used as an agent to inhibit, block or neutralize the activities of IL-17.

The in vivo and in vitro studies demonstrated the use of the anti-IL17A/F antibodies for manufacture of a medicament for the treatment of diseases associated with IL-17A and/or IL-17F in a subject. The diseases associated with IL-17A and/or IL-17F may be selected from autoimmune disorders or inflammatory diseases, for example, including, but not limited to, psoriasis, psoriatic arthritis, ankylosing spondylitis, rheumatoid arthritis (RA), multiple sclerosis (MS), systemic lupus erythematosus, osteoarthritis and inflammatory bowel disorder (IBD), and the like. The subject may be a mammal, such as rat, mouse, monkey, or human. Preferably, the subject is human.

The invention claimed is:

1. An anti-IL17A/F antibody that binds to both IL-17A and IL-17F and inhibits the activities of both IL-17A and IL-17F, wherein the antibody comprises a CDR1H represented by SEQ ID NO: 1, CDR2H represented by SEQ ID NO: 2, CDR3H represented by SEQ ID NO: 3; and CDR1L represented by SEQ ID NO: 4, CDR2L represented by SEQ ID NO: 5 and CDR3L represented by SEQ ID NO: 6.

2. The anti-IL17A/F antibody according to claim 1, wherein the antibody comprises a variable heavy chain domain (VH1-1) represented by SEQ ID NO: 7, and a variable light chain domain (VL5) represented by SEQ ID NO: 8 or VL2-1 represented by SEQ ID NO: 9.

3. The anti-IL17A/F antibody according to claim 1, wherein the antibody comprises a heavy chain represented by SEQ ID NO: 10, and a light chain represented by SEQ ID NO: 11.

4. The anti-IL17A/F antibody according to claim 1, wherein the antibody is of human IgG class.

5. The anti-IL17A/F antibody according to claim 1, wherein the antibody is a murine, chimeric or humanized antibody.

6. A pharmaceutical composition comprising the anti-IL 17A/F antibody according to claim 1, and a pharmaceutically acceptable excipient.

7. A method of treating a disease associated with IL-17A and/or IL-17F in a subject in need thereof, comprising administrating the anti-IL17A/F antibody according to claim 1.

8. The method according to claim 7, wherein the anti-IL17A/F antibody comprises a variable heavy chain domain (VH1-1) represented by SEQ ID NO: 7, and a variable light chain domain (VL5) represented by SEQ ID NO: 8 or VL2-1 represented by SEQ ID NO: 9.

9. The method according to claim 7, wherein the anti-IL17A/F antibody comprises a heavy chain represented by SEQ ID NO: 10, and a light chain represented by SEQ ID NO: 11.

10. The method according to claim 7, wherein the anti-IL17A/F antibody is a murine, chimeric or humanized antibody.

11. The method according to claim 7, wherein the disease associated with IL-17A and/or IL-17F is selected from autoimmune disorders or inflammatory diseases.

12. The method according to claim 11, wherein the disease is selected from psoriasis, psoriatic arthritis, ankylosing spondylitis, rheumatoid arthritis (RA), multiple sclerosis (MS), systemic lupus erythematosus, osteoarthritis or inflammatory bowel disorder (IBD).

13. The method according to claim 7, wherein the subject is a mammal.

14. The method according to claim 13, wherein the subject is selected from rat, mouse, monkey, or human.

15. The method according to claim 14, wherein the subject is human.

* * * * *

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial sequence
<220> FEATURE:
<223> OTHER INFORMATION: CDR1H amino acid sequence

<400> SEQUENCE: 1

Asp Tyr Asn Leu Asn
1               5

<210> SEQ ID NO 2
<211> LENGTH: 17
<212> TYPE: PRT
<213> ORGANISM: Artificial sequence
<220> FEATURE:
<223> OTHER INFORMATION: CDR2H amino acid sequence

<400> SEQUENCE: 2

Val Ile His Pro Asp Tyr Gly Thr Thr Ser Tyr Asn Gln Lys Phe Lys
1               5                   10                  15

Asp

<210> SEQ ID NO 3
<211> LENGTH: 9
<212> TYPE: PRT
<213> ORGANISM: Artificial sequence
<220> FEATURE:
<223> OTHER INFORMATION: CDR3H amino acid sequence

<400> SEQUENCE: 3

Tyr Asp Tyr Gly Asp Ala Met Asp Tyr
1               5

<210> SEQ ID NO 4
<211> LENGTH: 16
<212> TYPE: PRT
<213> ORGANISM: Artificial sequence
```

```
<220> FEATURE:
<223> OTHER INFORMATION: CDR1L amino acid sequence

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial sequence
<220> FEATURE:
<223> OTHER INFORMATION: CDR2L amino acid sequence

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial sequence
<220> FEATURE:
<223> OTHER INFORMATION: CDR3L amino acid sequence

<400> SEQUENCE: 6

Ser Gln Ser Thr His Val Pro Leu Thr
1               5

<210> SEQ ID NO 7
<211> LENGTH: 118
<212> TYPE: PRT
<213> ORGANISM: Artificial sequence
<220> FEATURE:
<223> OTHER INFORMATION: Variable heavy chain domain (VH1-1) amino acid
      sequence

<400> SEQUENCE: 7

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asn Trp Val Arg Gln Ala Pro Gly Lys Gly Leu Glu Trp Met
        35                  40                  45

Gly Val Ile His Pro Asp Tyr Gly Thr Thr Ser Tyr Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Tyr Asp Tyr Gly Asp Ala Met Asp Tyr Trp Gly Gln Gly Thr
            100                 105                 110

Leu Val Thr Val Ser Ser
        115

<210> SEQ ID NO 8
<211> LENGTH: 112
<212> TYPE: PRT
<213> ORGANISM: Artificial sequence
<220> FEATURE:
<223> OTHER INFORMATION: Variable light chain domain (VL5) amino acid
      sequence
```

<400> SEQUENCE: 8

Asp Ile Val Met Thr Gln Ser Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Pro
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Leu Glu Ile Lys
            100                 105                 110

<210> SEQ ID NO 9
<211> LENGTH: 112
<212> TYPE: PRT
<213> ORGANISM: Artificial sequence
<220> FEATURE:
<223> OTHER INFORMATION: Variable light chain domain (VL2-1) amino acid
      sequence

<400> SEQUENCE: 9

Asp Ile Val Met Thr Gln Thr Pro Leu Ser Ser Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Leu Gln Gln Arg Pro Gly Gln Pro
        35                  40                  45

Pro Arg Leu Leu Ile Tyr Lys Val Ser Asn Arg Phe Ser Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Leu Glu Ile Lys
            100                 105                 110

<210> SEQ ID NO 10
<211> LENGTH: 448
<212> TYPE: PRT
<213> ORGANISM: Artificial sequence
<220> FEATURE:
<223> OTHER INFORMATION: Heavy chain amino acid sequence comprising
      VH1-1

<400> SEQUENCE: 10

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asn Trp Val Arg Gln Ala Pro Gly Lys Gly Leu Glu Trp Met
        35                  40                  45

Gly Val Ile His Pro Asp Tyr Gly Thr Thr Ser Tyr Asn Gln Lys Phe
50                  55                  60

```
Lys Asp Arg Val Thr Met Thr Val Asp Thr Ser Thr Val Tyr
 65                  70                  75                  80

Met Glu Leu Ser Ser Leu Arg Ser Glu Asp Thr Ala Val Tyr Tyr Cys
             85                      90                  95

Val Arg Tyr Asp Tyr Gly Asp Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 11
<211> LENGTH: 219
<212> TYPE: PRT
<213> ORGANISM: Artificial sequence
<220> FEATURE:
<223> OTHER INFORMATION: Light chain amino acid sequence comprising VL5
```

```
<400> SEQUENCE: 11

Asp Ile Val Met Thr Gln Ser Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Pro
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```